US010376617B2

(12) United States Patent
Giezendanner et al.

(10) Patent No.: US 10,376,617 B2
(45) Date of Patent: Aug. 13, 2019

(54) SUSPENSION DEVICE OF A DRAINAGE CONTAINER (71) Applicant: MEDELA HOLDING AG, Baar (CH)

(72) Inventors: Charles Giezendanner, Morschach (CH); Cornel Bächler, Gisikon (CH); Hilmar Ehlert, Hergiswil (CH)

(73) Assignee: MEDELA HOLDING AG, Baar (CH)

(*) Notice: Subject to any disclaimer, the term of this patent is extended or adjusted under 35 U.S.C. 154(b) by 131 days.

(21) Appl. No.: 15/508,396

(22) PCT Filed: Aug. 28, 2015

(86) PCT No.: PCT/EP2015/069755
§ 371 (c)(1),
(2) Date: Mar. 2, 2017

(87) PCT Pub. No.: WO2016/034510
PCT Pub. Date: Mar. 10, 2016

(65) Prior Publication Data
US 2017/0281836 A1 Oct. 5, 2017

(30) Foreign Application Priority Data
Sep. 2, 2014 (EP) .................................. 14183201

(51) Int. Cl.
*A61M 1/00* (2006.01)
*G01F 22/00* (2006.01)
(Continued)

(52) U.S. Cl.
CPC ......... *A61M 1/0001* (2013.01); *A61G 13/102* (2013.01); *G01F 22/00* (2013.01);
(Continued)

(58) Field of Classification Search
CPC ............ A61M 1/0001; A61M 2205/18; A61M 2205/3393; A61M 2209/082;
(Continued)

(56) References Cited

U.S. PATENT DOCUMENTS 374,759 A 12/1887 Segog
2,478,272 A 8/1949 Jennings
(Continued)

FOREIGN PATENT DOCUMENTS

CN 201897492 U 7/2011
CN 202158898 U 3/2012
(Continued)

OTHER PUBLICATIONS

International Search Report for Application No. PCT/EP2015/069755, dated Dec. 4, 2015.
(Continued)

*Primary Examiner* — Marrit Eyassu
(74) *Attorney, Agent, or Firm* — Marshall, Gerstein & Borun LLP (57) ABSTRACT A suspension device for a drainage container has, on a first side, a first fastening unit for mounting and fastening the drainage container on the suspension device. On a second side, a second fastening unit is present for mounting and fastening the suspension device on a rail. The first fastening unit is arranged in a first fastening part, and the second fastening unit is arranged in a second fastening part. The suspension device further comprises a weighing part with a weighing element, wherein the weighing part is connected or can be connected to the first fastening part and to the second fastening part so as to measure, with the weighing element, a relative displacement, such that a filling quantity of the aspirated body fluid in the drainage container can be determined.

13 Claims, 5 Drawing Sheets (51) Int. Cl.
*A61G 13/10* (2006.01)
*A61G 7/05* (2006.01)

(52) U.S. Cl.
CPC ........ *A61G 7/0503* (2013.01); *A61G 2203/44* (2013.01); *A61M 2205/18* (2013.01); *A61M 2205/3393* (2013.01); *A61M 2209/082* (2013.01)

(58) Field of Classification Search
CPC ................ A61G 13/102; A61G 7/0503; A61G 2203/44; G01F 22/00
USPC .......................................................... 73/296
See application file for complete search history.

(56) References Cited

U.S. PATENT DOCUMENTS

| | | | | |
|---|---|---|---|---|
| 4,712,567 A | * | 12/1987 | Gille | A61B 5/14507 600/573 |
| 5,458,566 A | * | 10/1995 | Herrig | A61M 1/3624 128/DIG. 13 |
| 5,756,940 A | | 5/1998 | Van Driel et al. | |
| 2007/0106177 A1 | | 5/2007 | Hama | |
| 2010/0089152 A1 | | 4/2010 | Kolada et al. | |
| 2013/0165877 A1 | | 6/2013 | Leeson et al. | |
| 2013/0197471 A1 | * | 8/2013 | Williams | A61M 3/0229 604/500 |
| 2017/0203028 A1 | * | 7/2017 | Carr | A61M 3/0254 |

FOREIGN PATENT DOCUMENTS

| | | | |
|---|---|---|---|
| CN | 202599512 U | 12/2012 | |
| DE | 20217847 U1 | 4/2004 | |
| DE | 202010010088 U1 | 10/2010 | |
| WO | WO-9421311 A2 | 9/1994 | |
| WO | WO-97/10856 A1 | 3/1997 | |
| WO | WO 9710856 A1 * | 3/1997 | .......... A61M 1/0001 |
| WO | WO 2004046666 A1 * | 6/2004 | .......... A61M 1/0019 |
| WO | WO-2007/085100 A2 | 8/2007 | |
| WO | WO-2013/177716 A1 | 12/2013 | |

OTHER PUBLICATIONS

International Preliminary Report on Patentability of the International Searching Authority for Application No. PCT/EP2015/069755, dated Mar. 16, 2017.

* cited by examiner

SUSPENSION DEVICE OF A DRAINAGE CONTAINER

CROSS-REFERENCE TO RELATED APPLICATION

The present application is the US national phase of International Application No. PCT/EP2015/069755, filed Aug. 28, 2015, which application claims priority to European Application No. 14183201.4, filed Sep. 2, 2014. The priority application, EP 14183201.4, is hereby incorporated by reference.

TECHNICAL FIELD

The present invention relates to a suspension device for a drainage container, a fastening mechanism of such a suspension device, a fastening part of such a suspension device, and a drainage system with such a suspension device.

PRIOR ART

Drainage containers, also called fluid collection containers, are containers for collecting body fluids which are obtained during suction in the context of medical and cosmetic treatments. The body fluid is conveyed into the container via a patient-side drainage line or suction line by means of a vacuum pump. For this purpose, the container has a port for the patient-side drainage line and a port for the suction pump or vacuum pump or for a central vacuum of the hospital. The drainage container can be a disposable container, or at least parts thereof can be used a number of times.

WO 2007/085100 and WO 2013/177716 disclose drainage containers with an outer container, a lid tightly closing this outer container, and a bag which is received in the outer container and is sealingly connected to the lid. The lid and the bag can be removed together from the outer container. These containers can be connected by means of a snap-fit connection to a suspension device, which in turn can be fastened to a rail. The rail is preferably a wall rail of the hospital or of the nursing unit or a bed rail. This suspension device has a main body which is provided, on one side, with a spring-loaded clip for clamping on the rail and, on the opposite side, with a vertically extending slot. The outer container has a slot insert which correspondingly extends in the vertical direction and which can be pushed into the slot. The lid with the bag is intended to be disposed of after one use. The drainage container can be used again but only for a limited number of times. By contrast, the suspension device is in use for several years and is also used for fastening other medical devices. These drainage containers and these suspension devices have proven useful in practice.

The filling level of the drainage containers has to be regularly checked, on the one hand because it provides an indication of the success of the drainage and on the other hand because it should not be exceeded. In the prior art, this check is made visually by the nursing staff. This is made difficult, if not impossible, if the fluid is not collected directly in a rigid container with a filling indicator but instead in a bag. There is therefore a need to provide drainage containers of this kind with a device for measuring the filling quantity.

The determination of filling quantities is known in other fields. Thus, CN 20259912 U describes a beaker which has a handle and in which a cup can be suspended. A weighing sensor is present in the handle in order to determine the weight of the cup and of the contents of the latter.

CN 201897492 U discloses a jug with a handle which is connected rigidly thereto and which again has a weighing sensor.

CN 202158898 U discloses a ring-shaped base plate with a weighing device on which a handle is integrally formed. A jug can be placed on this base plate.

US 2010/0089152 and DE 20 2010 010 088 U disclose a jug with a handle, and a base plate with a weighing device.

In U.S. Pat. No. 374,759 and U.S. Pat. No. 2,478,272, movable mechanical displays are used to indicate the filling quantity of a container.

DISCLOSURE OF THE INVENTION

It is an object of the invention to make it easier to determine a filling quantity of a drainage container.

The suspension device according to the invention for a drainage container that is used to collect aspirated body fluid has, on a first side, a first fastening unit for mounting and fastening the drainage container, preferably the outer container thereof, on the suspension device, and has, on a second side, a second fastening unit for mounting and fastening the suspension device on a rail. The first fastening unit is arranged in a first fastening part, and the second fastening unit is arranged in a second fastening part. The suspension device comprises a weighing part with a weighing element, wherein the weighing part is connected or can be connected to the first fastening part and to the second fastening part so as to measure, with the weighing element, a relative displacement between the first fastening part and the second fastening part, such that a filling quantity of the aspirated body fluid in the drainage container can be determined. The second side is preferably arranged adjacent to or opposite the first side.

By virtue of the fact that the measurement takes place in the suspension device and not in the container itself, it is also possible to precisely determine the filling quantity or the weight of the contents of a bag.

Furthermore, this has the advantage that containers that can be used only for a limited time can still be produced cost-effectively, and the electronic parts are integrated in the reusable suspension device. This is particularly the case when the first fastening unit is designed to produce a releasable connection to the drainage container, preferably to the outer container thereof, in the intended use of the suspension device.

Alternatively or in addition, the second fastening unit is also preferably designed to produce a releasable connection to the rail in the intended use of the suspension device.

In an alternative embodiment, however, the suspension device or at least the first fastening part and the weighing part are rigidly connected to the drainage container, in particular the outer container.

In a preferred embodiment, the first fastening part and the weighing part form a rigidly interconnected unit and are not designed to be separated from each other in the intended use of the suspension device.

In this text, intended use is understood as a use which serves to aspirate body fluid from a patient and which requires, for this purpose, that the drainage container is correctly fastened in order to achieve this. The connections can be produced and/or released before or after the aspiration. A separation during the suctioning is preferably likewise possible. The connection can be produced and released preferably without the need for any tools, and instead it can preferably be done by hand.

Preferably, the second fastening part forms a releasable connection to the weighing part in the intended use of the suspension device. This has the advantage that the fastening part can also be used to fasten other devices. In particular, a second fastening part of the kind described in WO 2007/085100 can be used.

In another embodiment, the second fastening part and the weighing part form a rigidly interconnected unit and are not designed to be separated from each other during use, as a result of which the first fastening part, the weighing part and the second fastening part form a unit that is not designed to be separated during use. This has the advantages that the suspension device is very compact, despite the integrated weighing element, and relatively inexpensive and also that individual parts cannot be lost.

The weighing element is in particular a weighing cell, a spring element with displacement measurement, a piezo-electric sensor or a pressure sensor with linear guide.

In a preferred embodiment, the weighing element, in particular the weighing cell, has a first area which is rigidly connected to the first fastening part, wherein the weighing element has a second area which is rigidly connected to the weighing part. In this way, the second fastening part can be designed relatively freely, and it can be connected in particular to the weighing part by a connection that is releasable during use.

Preferably, the second fastening part has an overload protection. The latter is formed by a spring-loaded bolt which is displaceable in the vertical direction and on which the weighing part bears. Preferably, or alternatively, the second fastening part has a projection which extends as far as the first fastening part and which serves to support the first fastening part in the event of a weight overload. These embodiments permit an overload protection which prevents an overloading of the weighing element, in particular an overextension of strain gauges of the weighing cell.

To be able to perform the weight determination as precisely as possible, the suspension device preferably has a strain relief means for a drainage hose which is connected to the drainage container and which is used to aspirate the body fluid. This drainage hose is preferably suspended. Preferably, the strain relief means has a bracket which is supported by the weighing part and/or by the second fastening part and which in turn supports the drainage hose.

The suspension device defines a suspension axis for the suspension of the drainage container, and, in a preferred embodiment, a tilt sensor is present for determining an angle between the suspension axis and a vertical within the room in which the suspension device is located. In this way, it is possible to establish whether the rail, and therefore the drainage container, is at an inclination, and it is thereby possible to compensate electronically for any measuring errors that result from this. Alternatively or in addition, a warning can also be provided if the container hangs at an inclination and threatens to topple over.

Preferably, the suspension device has a display for showing the measured filling quantity, such that the nursing staff, the medical specialists or even the patients can read off the measured values on the spot. Depending on the embodiment, an acoustic and/or visual signal transmitter is provided that warns of a threat of overfilling.

In a preferred embodiment, the suspension device has an electronics unit for transmitting the defined filling quantity and/or a warning signal to an external receiver. This external receiver can be the vacuum pump, a controller of the central vacuum or a valve unit for the central vacuum. Preferably, the external receiver is a clinical network. Preferably, the measured values are entered directly into the patient data and/or generate a warning signal in the nursing staff ward room.

It is also possible for several drainage containers to be connected one behind another or side by side, in which case the measured values of all the drainage containers are totalled and are shown on a common display on site. Alternatively or in addition, the signals can also be delivered jointly to an external receiver.

The measured values can be further processed. It is thus possible to determine the flow rate. When suction is performed at several locations on the patient, e.g. in liposuction, a comparison can be made between the different amounts of fluid that are aspirated.

Parts of the suspension device can also be produced and sold individually. For example, a fastening mechanism of the suspension device according to the invention has a first fastening part with a first fastening unit for mounting and fastening the drainage container on the suspension device, and it further comprises a weighing part with a weighing element. The weighing part is connected to the first fastening part, and the weighing part can be connected to a second fastening part for the purpose of connection to a rail, so as to measure, with the weighing element, a relative displacement between the first and second fastening parts such that a filling quantity of the aspirated body fluid in the drainage container can be determined.

Moreover, a second fastening part of the suspension device according to the invention can be produced and sold individually. This second fastening part has a second fastening unit for connecting the suspension device to a rail. It has a weight overload protection, wherein the weight overload protection has a spring-loaded bolt for supporting the weighing part. Alternatively or in addition, a projection can be present on which the first fastening part bears in the event of an overload.

In a preferred embodiment, the suspension device according to the invention, together with a drainage container, forms a drainage system. The drainage container has an outer container, a bag to be received in the outer container, and a lid tightly closing the outer container. The bag is connected sealingly to the lid and can be removed together with the lid from the outer container. The outer container moreover has a fastening unit for connecting to the first fastening unit of the first fastening part. However, the suspension device according to the invention can also be used with different types of drainage containers, in particular those without a bag.

BRIEF DESCRIPTION OF THE DRAWINGS

A preferred embodiment of the invention is described below with reference to the drawings, which serve only for illustration and are not to be interpreted as limiting the invention. In the drawings.

DESCRIPTION OF PREFERRED EMBODIMENTS

Figure 1:
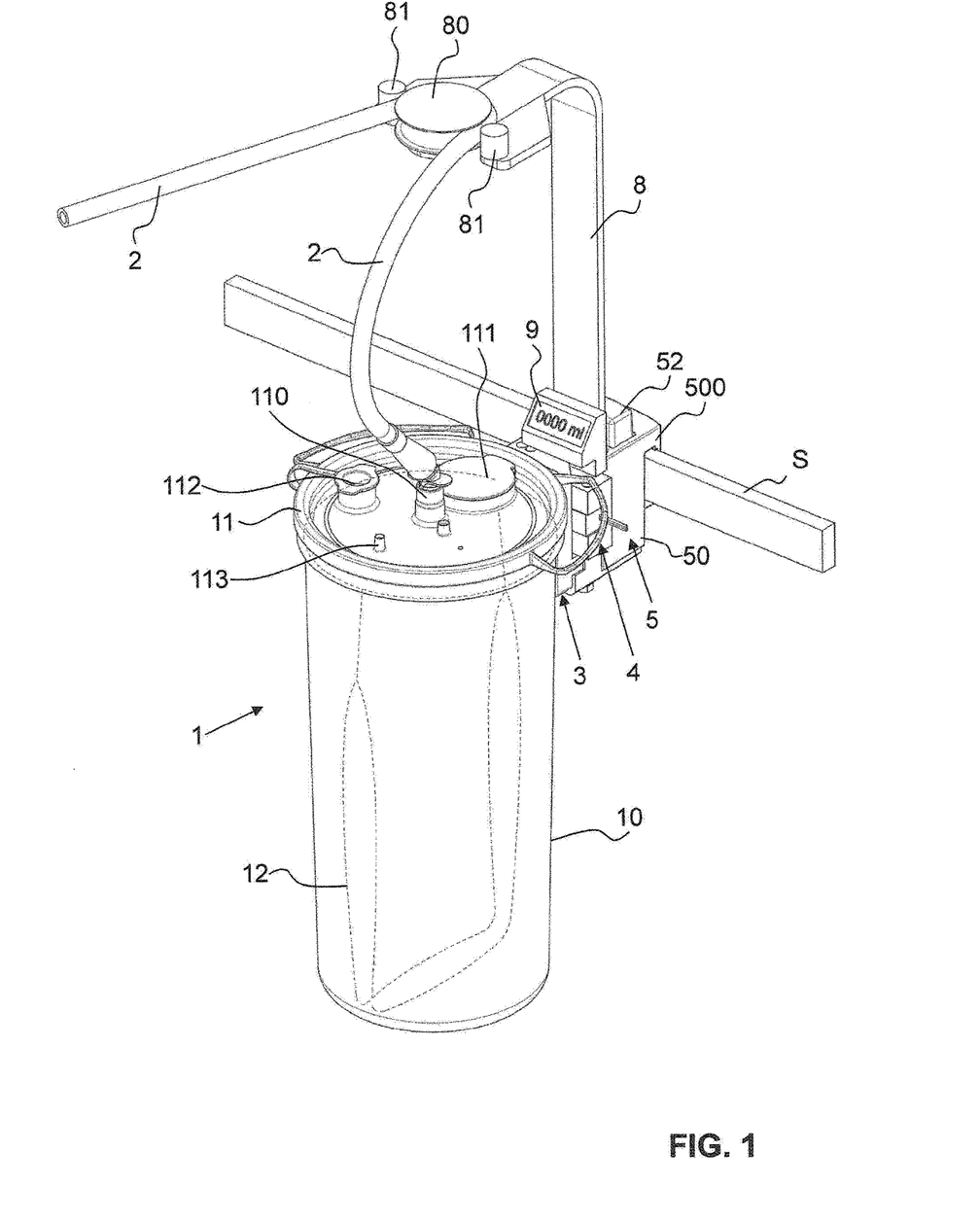
FIG. 1 shows a perspective view of a drainage system according to the invention.

FIG. 1 shows a drainage container 1 with a rigid, preferably transparent outer container 10, a lid 11 tightly closing the latter, and a bag 12 which is fastened sealingly on the lid 11 and is received in the outer container 10.

Figure 3:
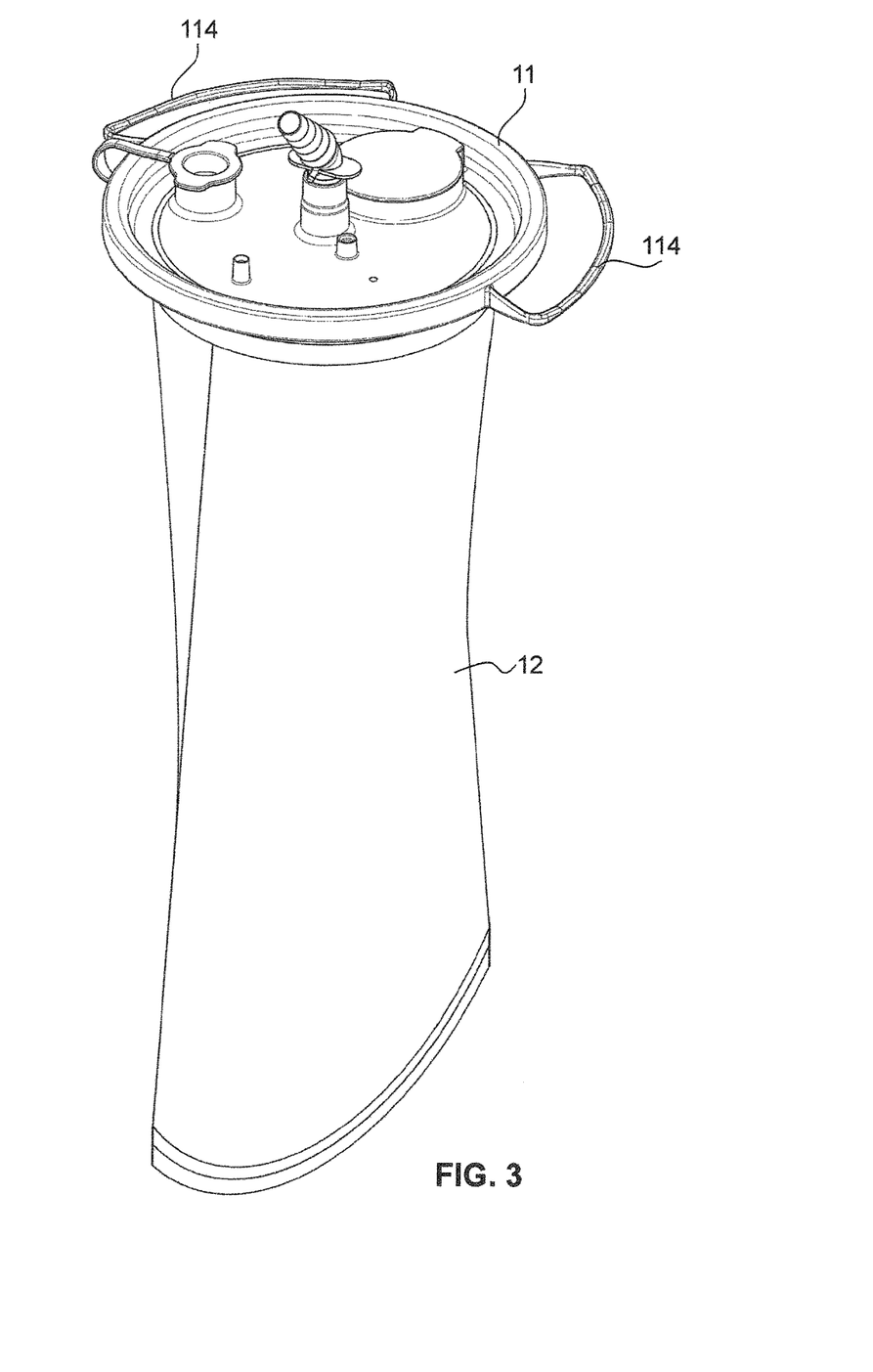
FIG. 3 shows a perspective view of a lid with a bag of the drainage system according to FIG. 1.

The container 1 has the usual means necessary for connection to the patient and to the vacuum source. These means are commonly known, for example from WO 2007/085100 and WO 2013/177716. A drainage port 110 for connecting the interior of the bag to a drainage hose 2 is present on the lid 11, wherein the drainage hose 2 leads to the patient and conveys the aspirated fluid into the container. Moreover, the lid 11 preferably has a serial port 112 such that it can be connected in series to a second drainage container. Reference number 113 designates a fastening stub, on which closure pieces can normally be fitted when the device is not in use. Reference number 111 designates a filter cover, which likewise leads to the interior of the bag but has a further channel which ends in the space between outer container and bag and which creates a connection to a lateral suction port in the outer container 10. The suction port serves for connection to the vacuum source. It is not visible here but is known from WO 2013/177716. Handgrips 114 make it easier to remove the lid 11 and the bag 12 from the outer container 10. The lid 11, with the bag 12 fastened to it, preferably adhesively bonded to it or welded to it, is shown in FIG. 3.

The drainage container 1, more specifically the outer container 10, is suspended laterally on a suspension device 3, 4, 5 and fastened thereto. The suspension device 3, 4, 5 can be mounted and fastened to a rail S, e.g. to a wall rail or to a bed rail. The suspension device 3, 4, 5 moreover carries an angled bracket 8, of which the vertical branch protrudes upwards above the rest of the suspension device 3, 4, 5 and of which the horizontal branch faces towards the drainage container 1. In this text, vertical relates to the position in which the device is intended to be used.

A guide roller 80 and two guide pins 81 flanking the latter are fastened to the free end of the horizontal branch. The drainage hose is held between the guide roller 80 and the guide pins 81 without being pressed together. The bracket 8 thus forms a strain relief means and bears the weight of the drainage hose 2 leading from the guide roller 80 to the patient.

Figure 2:
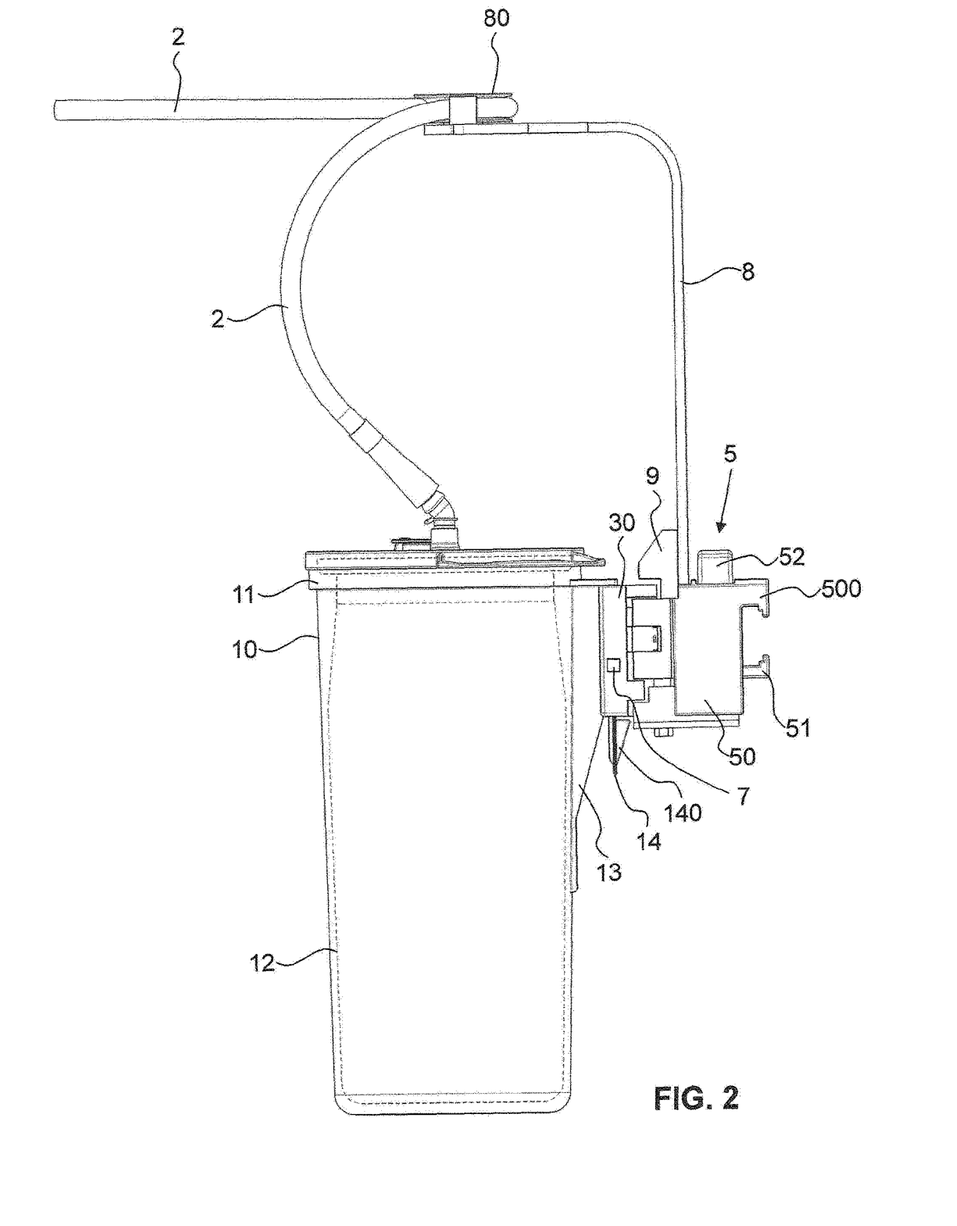
FIG. 2 shows a side view of the drainage system according to FIG. 1.

As can be seen clearly in FIG. 2, the outer container 10 has a laterally protruding fastening piece 13 with a slot insert. A spring element 14 with a retaining lug 140 is arranged on the slot insert, wherein the spring element forms a downwardly directed continuation of the vertically extending slot insert. This also corresponds to the container according to WO 2007/085100.

This slot insert is pushed into a first slot 31 (FIG. 4) of a container-side fastening part 3 of the suspension device according to the invention and is fixed in its position with the spring-loaded retaining lug 140. In this way, the container 1 is suspended on this first container-side fastening part 3. In this example, the first slot 31 forms a first fastening unit.

The suspension device moreover has a second, rail-side fastening part 5. The latter has a substantially cuboid main body 50, on which an upper stationary claw 500 is integrally formed. The claw 500 is located on the side directed away from the first fastening part 3. A claw 51 held movably in the main body 50 forms a mating piece to the stationary claw 500. The movable claw 51 can be actuated by means of a spring-loaded push button 52, which protrudes from an upper face of the main body 50. By means of this second fastening unit, namely the two claws 500, 51, it is possible for the second fastening part 5 and therefore the rest of the suspension device, and also the drainage container 1, to be fastened to the rail S.

To measure the filling quantity in the bag 12, in particular to determine the weight thereof, the suspension device has a weighing part 4 between the first and second fastening parts 3, 5. A display 9 shows the measured filling quantity, here in milliliters (ml). Other kinds of indications, e.g. weight indications or graphic displays of a filling level or of a filling profile, are also possible.

Figures 4, 5:
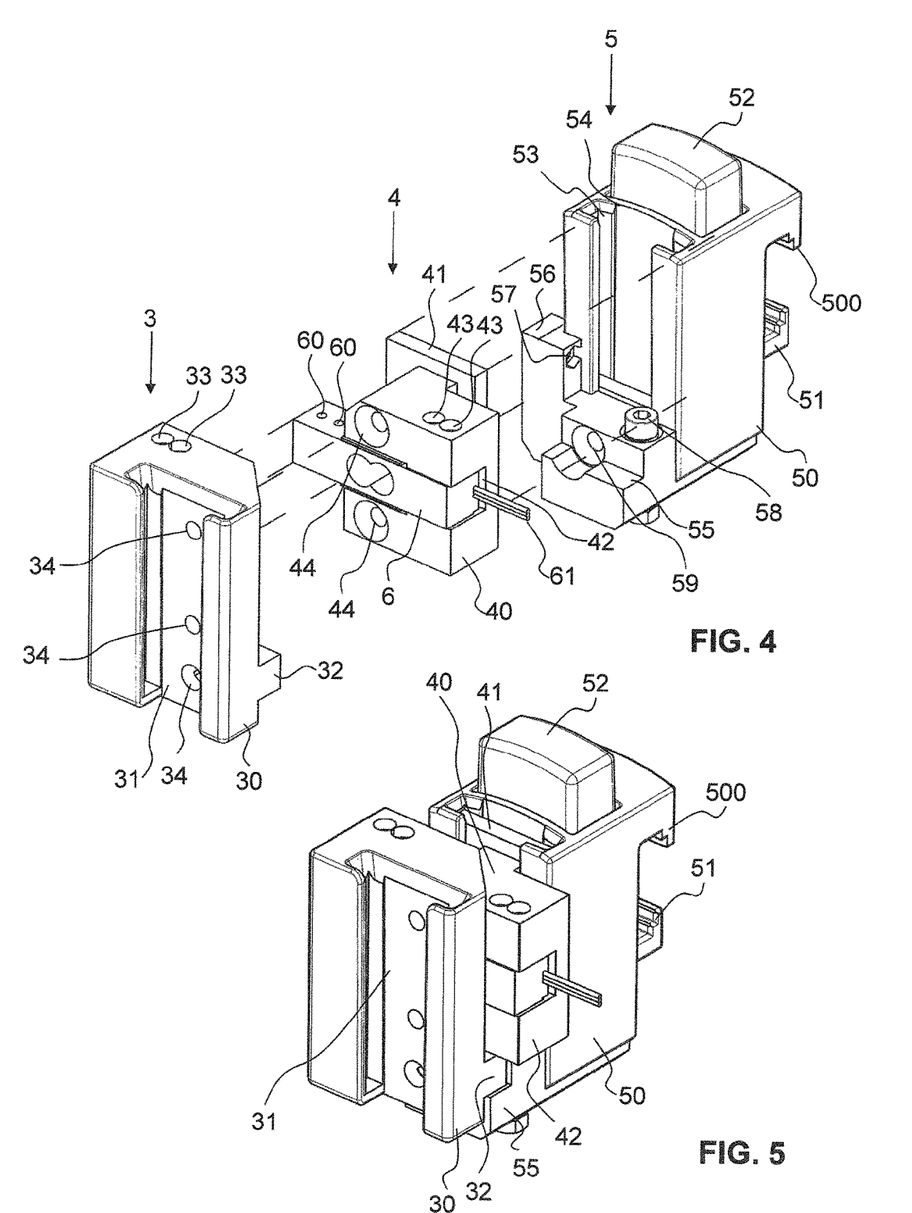
FIG. 4 shows an exploded view of a suspension device of the drainage system according to FIG. 1.
FIG. 5 shows a perspective view of the suspension device according to FIG. 4 in the assembled state.

The individual parts of the suspension device according to the invention are described in more detail below with reference to FIGS. 4 and 5.

The first, container-side fastening part 3 has a substantially cuboid main body 30. Its side facing towards the container 1 is provided with the aforementioned vertically extending first slot 31. At the bottom of the first slot 31, through-holes 34 are provided which permit access for fastening screws in the following weighing part 4. The upper face of the main body 30 has at least one fastening hole, here two fastening holes 33. They are located in an edge area of the upper face and serve for rigid connection to a weighing element 6, here a weighing cell. The latter for this purpose has corresponding fastening holes 60. Preferably, the container-side fastening part 3 is screwed onto the weighing cell 6. However, other fastening options are also possible.

On the side of the main body 30 directed away from the container 1, the container-side fastening part 3 has, in its lower area, a first projection 32, which faces towards the second, rail-side fastening part 5. Said side of the main body 30 directed away from the container is otherwise preferably plane and is designed extending in the vertical direction in the position of use.

The weighing part 4 likewise has a substantially cuboid main body 40 with a second slot 42 which extends in the horizontal direction. The weighing cell 6 is held in this second slot 42, wherein the weighing cell 6 protrudes from at least one end of the second slot 42 and is connected at this end to the container-side fastening part 3. At its other end, the weighing cell 6 is rigidly connected to the main body 40 of the weighing part 4. For this purpose, the main body 40 has fastening holes 43 on its upper face, preferably in an edge area. Here too, the rigid connection between main body 40 and weighing cell 6 is preferably effected by screwing, although other fastening options are also possible here.

Known means can be used as the weighing cell 6. These are usually measuring means with strain gauges. Reference number 61 designates the cable running from the weighing cell 6 to electronics (not shown) and, if appropriate, to a source of electrical energy. It is also possible to arrange all or some of the electronics in the weighing part 4. In preferred embodiments, data are transmitted not only to a display but also to external receivers. In other embodiments, there is no display. Furthermore, it is possible to equip the weighing part with an acoustic signal transmitter, which can be activated according to the measured filling value. Instead of the weighing cell 6, a spring element with displacement measurement, a piezoelectric sensor or a pressure sensor with a linear guide can also be used.

On the side of the main body 40 directed away from the slot 42, a vertically extending slot insert 41 is present. It is preferably formed integrally on the main body 40. This slot insert 41 can be brought into engagement with a third slot 53, which is integrally formed in the main body 50 of the second, rail-side fastening part 5. At its lower side, this third slot 53 ends in a double step, wherein a spring-loaded bolt 58 protrudes from the upper step and is movable in the vertical direction counter to the spring force. The weighing part 4 bears on this bolt 58. The spring force must be chosen such that the bolt 58, and therefore the bearing surface of the weighing part 4, is not pressed downwards under a normal load, i.e. with normal filling of the drainage container.

At the lateral end of this upper step lying opposite the bolt 58, a side wall 56 rises up. It is preferably formed in one piece together with the steps. It has a continuous threaded hole 57. A screw (not shown here) that is screwed through this threaded hole engages in a lateral vertical slot of the weighing part 4 and thus fixes the weighing part 4 on the rail-side fastening part 5. The weighing part 4 is still displaceable in the vertical direction along the connection between slot and slot insert. If no screw is inserted, the weighing part 4 is also releasable from the rail-side fastening part 5 by hand without using tools.

If the double step is a separate structural part, it can be connected, for example by means of a screw connection, to the main body 50 of the rail-side fastening part 5. The corresponding threaded hole 59 can be clearly seen in FIG. 4. This variant has the advantage that the known suspension devices can be used as the main body 50 of the rail-side fastening part 5. However, it is also possible for the main body 50 to be configured in one piece with the double step and the side wall 56.

The lower step of the second, rail-side fastening part 5 forms a second projection 55 which, in the assembled state of the individual parts, extends as far as the first, container-side fastening part 3 and comes to lie at a distance underneath the first projection 32 of the container-side fastening part 3. The distance is determined by the bolt 58.

The two fastening parts 3, 5 and the weighing part 4 are preferably made substantially of plastic, preferably by injection moulding.

In its intended use, the suspension device is joined together. The rail-side fastening part 5 is clamped to the rail S, and the container 1 is suspended on the container-side fastening part 3. If the container, or more precisely the bag 12, is filled with aspirated body fluid, the container-side fastening part 3 is also pressed downwards. The rail-side fastening part and the weighing part 4 remain unaffected by this, however. The weighing cell 6 is thus bent, and its flexion yields a measurement value for the filling level.

In the event of an overloading of the first, container-side fastening part 3, the spring force of the bolt 58 is no longer sufficient to hold the weighing part 4 in position. The latter is likewise pressed down, but only so far that the projection 32 of the container-side fastening part 3 bears on the projection 55 of the rail-side fastening part 5.

Figures 6, 7:
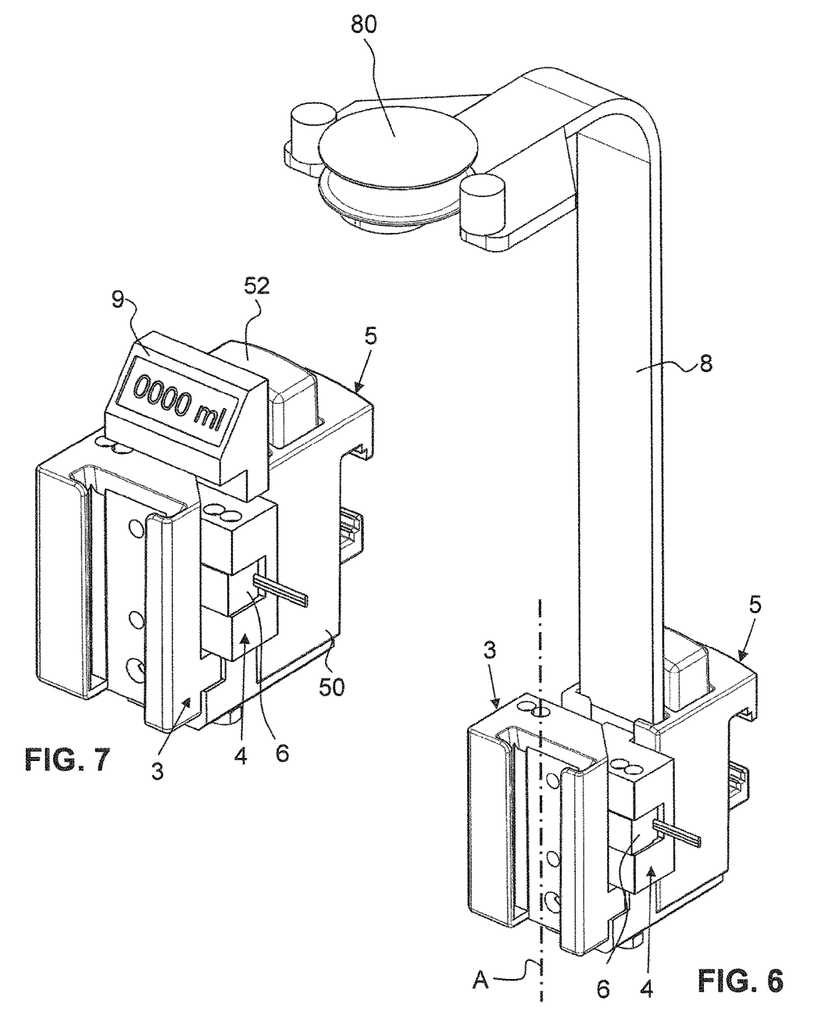
FIG. 6 shows a perspective view of the suspension device according to FIG. 4 with a strain relief means.
FIG. 7 shows a perspective view of the assembled suspension device with display.

It will be seen from FIG. 6 how the bracket 8 of the strain relief means is integrated into the suspension device. In a simple embodiment, it can be connected rigidly, and non-releasably during use, to the weighing part 4 or to the rail-side fastening part 5. Preferably, however, behind the third slot 53 of the rail-side fastening part 5, there is a likewise vertically extending fourth slot 54, into which a free end of the bracket 8 can be pushed and the bracket 8 can thus be held. A suspension axis A, which is defined by the suspension device, is likewise shown. If the rail S runs horizontally, the suspension axis A then runs vertically. Otherwise, it forms an angle to the vertical. The above-described directions of the individual parts relate to the case where the suspension axis A runs vertically. Otherwise, the described directions are to be understood as being parallel to the suspension axis A.

It will be seen from FIG. 7 that the display 9 is also added on. It can be fastened to any of the described parts.

A tilt sensor 7 may also be present, which serves to detect an inclined position of the container. It can establish if there is a threat of the container tipping over and/or can detect an inclined position of the rail, so that suitable corrections may be made in the measurement. The tilt sensor is preferably arranged as close as possible to the container, for example in the main body 30 of the container-side fastening part 3. It can also be integrated in the electronics. For example it is a gyro sensor.

The suspension device according to the invention permits, by simple means, a determination of a filling quantity of a drainage container, in particular of a drainage container with drainage bag.

What is claimed is:

1. A suspension device for a drainage container that is used to collect aspirated body fluid, wherein the suspension device has, on a first side, a first fastening unit for mounting and fastening the drainage container on the suspension device, and wherein the suspension device has, on a second side, a second fastening unit for mounting and fastening the suspension device on a rail, wherein the first fastening unit is arranged in a first fastening part, and the second fastening unit is arranged in a second fastening part, and wherein the second fastening part has a projection which extends as far as the first fastening part and which serves to support the first fastening part in the event of a weight overload, and wherein the suspension device comprises a weighing part with a weighing element, wherein the weighing part is connectable to the first fastening part and to the second fastening part so as to measure, with the weighing element (6), a relative displacement between the first fastening part and the second fastening part (5), such that a filling quantity of the aspirated body fluid in the drainage container is determined, wherein the suspension device defines a suspension axis for the suspension of the drainage container, wherein the suspension device has a tilt sensor for determining an angle between the suspension axis and a vertical within the room in which the suspension device is located, and electronically compensating for any measuring errors of the weighing element that result from said angle between the suspension axis and the vertical based on the angle as determined by the tilt sensor.

2. The suspension device according to claim 1, wherein at least one of the first fastening unit is configured to produce a releasable connection to the drainage container in the intended use of the suspension device, and the second fastening unit is configured to produce a releasable connection to the rail in the intended use of the suspension device.

3. The suspension device according to claim 1, wherein the first fastening part and the weighing part form a rigidly interconnected unit and are not configured to be separated from each other in the intended use of the suspension device.

4. The suspension device according to claim 3, wherein the second fastening part forms a releasable connection to the weighing part in the intended use of the suspension device.

5. The suspension device according to claim 3, wherein the second fastening part and the weighing part form a rigidly interconnected unit and are not configured to be separated from each other during use, as a result of which the first fastening part, the weighing part and the second fastening part form a unit that is not configured to be separated during use.

6. The suspension device according to claim 1, wherein the weighing element has a first area which is rigidly connected to the first fastening part, and wherein the weighing element has a second area which is rigidly connected to the weighing part.

7. The suspension device according to claim 1, wherein the suspension device moreover has a strain relief means for a drainage hose which is connected to the drainage container and which is used to aspirate the body fluid.

8. The suspension device according to claim 7, wherein the strain relief means has a bracket which is supported by at least one of the weighing part and the second fastening part.

9. The suspension device according to claim 1, wherein the suspension device moreover has a display for showing the determined filling quantity.

10. The suspension device according to claim 1, wherein the suspension device moreover has an electronics unit for transmitting the determined filling quantity to an external receiver.

11. The second fastening part of a suspension device according to claim 1, wherein the second fastening part has a second fastening unit for connecting the suspension device to a rail, wherein the second fastening part has a weight overload protection which is formed by a displaceable spring-loaded bolt for supporting the weighing part.

12. The drainage system with a drainage container and with a suspension device according to claim 1, wherein the drainage container has an outer container, a bag to be received in the outer container, and a lid tightly closing the outer container, wherein the bag (12) is connected sealingly to the lid and is removed together with the lid from the outer container, and wherein the outer container moreover has a fastening unit for connecting to the first fastening unit of the first fastening part.

13. A fastening mechanism of a suspension device for a drainage container that is used to collect aspirated body fluid, the suspension device defining a suspension axis for the suspension of the drainage container, wherein the fastening mechanism has a first fastening part with a first fastening unit for mounting and fastening the drainage container on the suspension device, wherein the fastening mechanism has a weighing part with a weighing element, wherein the weighing part is connected to the first fastening part, wherein the weighing part is connected to a second fastening part for the purpose of connection to a rail, so as to measure, with the weighing element, a relative displacement between the first fastening part and the second fastening part such that a filling quantity of the aspirated body fluid in the drainage container is determined, and wherein the second fastening part has a projection which extends as far as the first fastening part and which serves to support the first fastening part in the event of a weight overload, and wherein the fastening mechanism has a tilt sensor for determining an angle between the suspension axis and a vertical within the room in which the suspension device is located, and electronically compensating for any measuring errors of the weighing element that result from said angle between the suspension axis and the vertical based on the angle as determined by the tilt sensor.

* * * * *